United States Patent
Fukushi

[11] Patent Number: 5,834,630
[45] Date of Patent: Nov. 10, 1998

[54] APPARATUS FOR MEASURING FLASH POINT OF ARTICLE

[75] Inventor: Yoshiaki Fukushi, Tokyo, Japan

[73] Assignee: Tanaka Scientific Limited, Tokyo, Japan

[21] Appl. No.: 802,569

[22] Filed: Feb. 19, 1997

[51] Int. Cl.[6] .............................. G01M 3/20; G01N 27/00
[52] U.S. Cl. ................................................. 73/36; 422/54
[58] Field of Search ...................... 73/36; 374/8; 422/54; 340/579

[56] References Cited

U.S. PATENT DOCUMENTS

| | | | |
|---|---|---|---|
| 3,984,205 | 10/1976 | Karas et al. | 422/54 |
| 3,985,509 | 10/1976 | Trone et al. | 422/54 |
| 4,182,740 | 1/1980 | Hartmann et al. | 422/54 |
| 4,211,746 | 7/1980 | Mees | 422/54 |
| 4,410,854 | 10/1983 | Kroneisen et al. | 422/54 |
| 4,965,048 | 10/1990 | Ogasawara | 422/54 |

Primary Examiner—Hezron E. Williams
Assistant Examiner—Jay L. Politzer
Attorney, Agent, or Firm—Varndell Legal Group

[57] ABSTRACT

A flash point measuring apparatus including a sample vessel 11 made of an electrically conductive material, a heating device 17 for heating a sample S contained in the sample vessel 11, an igniting heat source 13 arranged above the sample vessel and made of an electrically conductive material, a temperature detecting device 12 for detecting a temperature of the sample S contained in the sample vessel 11, and a current amplifier 15 connected to the sample vessel 11 serving as a cathode and the igniting heat source 13 serving as an anode. Each time a temperature of the sample S is increased by 2° C., the igniting heat source is moved in a horizontal plane above the sample surface at a predetermined speed. When a mixture of a vapor of the sample S and an air is ignited, a flame ion current flows between the sample vessel 11 and the igniting heat source 13. A flash point of the sample S is measured as a temperature of the sample at which the flame ion current is detected by the current amplifier 15.

4 Claims, 1 Drawing Sheet prior art      Fig.1
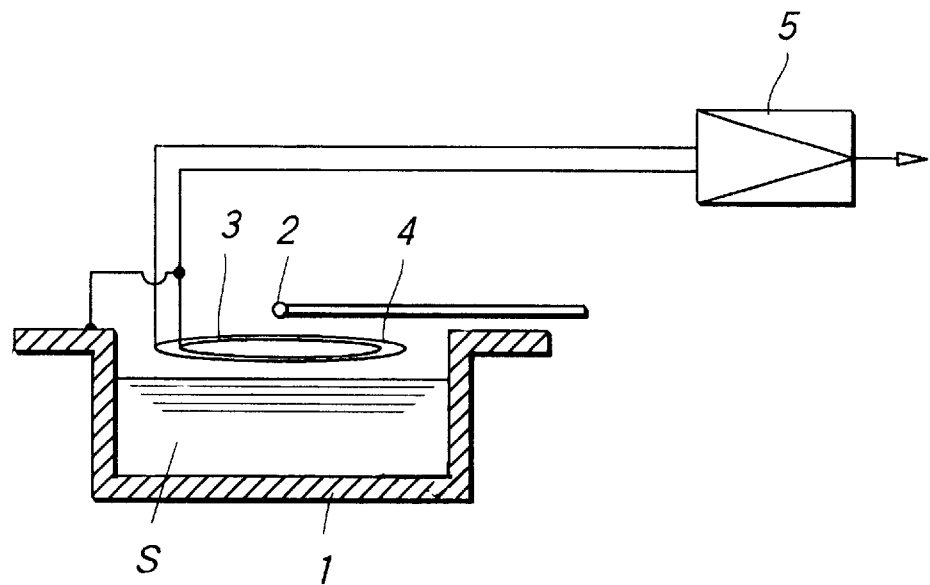
Fig.2
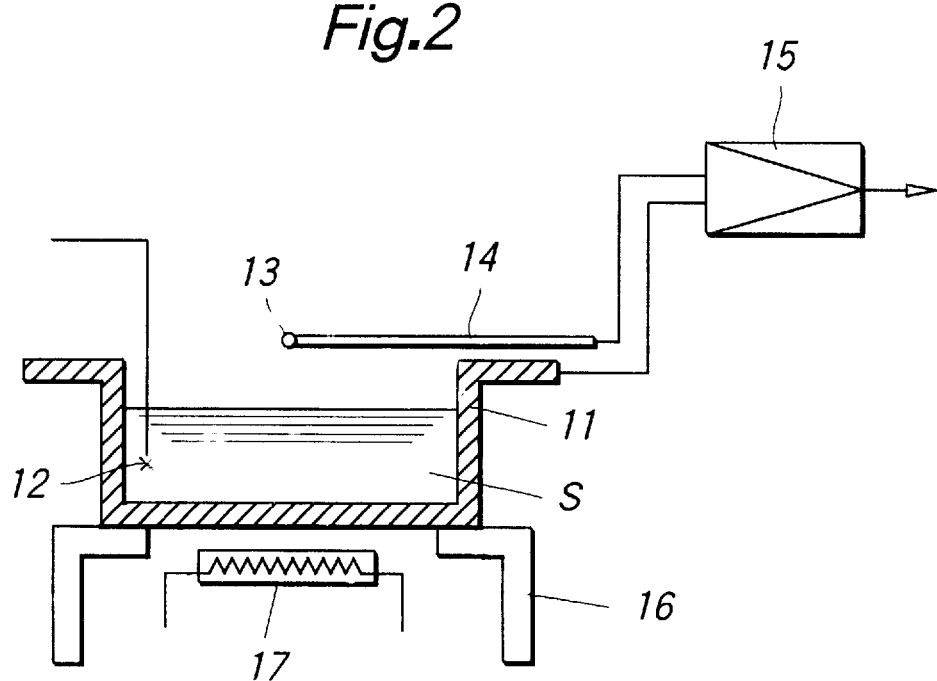

APPARATUS FOR MEASURING FLASH POINT OF ARTICLE

BACKGROUND OF THE INVENTION

1. Field of the Invention

The present invention relates to an apparatus for measuring a flash point of an article such as crude oil and other petroleum products.

2. Related Art Statement

There has been known a method of measuring a flash point of petroleum products such as gasoline and kerosene. For instance, a standard measuring method defined under D92(ASTM) has been established to measure a flash point of petroleum products. In this known method, a sample oil whose flash point is to be measured is heated under a given condition and a small test flame is brought near an oil surface. A flash point of the oil is measured by detecting a lowest temperature of the oil at which a mixed gas of an oil vapor and an air is ignited instantaneously with producing a flash.

There have been proposed various methods of detecting an igniting condition of a mixture of an oil vapor and an air, e.g. (1) an abrupt temperature change at the ignition is detected; (2) flash generated at the ignition is detected; and (3) a flame ion current produced at the ignition is detected.

FIG. 1 shows a known apparatus for measuring a flash point of an oil, in which an ignition is detected by the above mentioned flame ion current method (3). A sample vessel 1 having a wide opening is placed on a platform not shown and a sample oil S is contained in the vessel. Below the sample vessel 1, there is provided a heating device for heating the sample oil S contained in the sample vessel. The heating device may be formed by an electric heater or a gas burner, but in FIG. 1, the heating device is not shown for the sake of simplicity.

Above the sample vessel 1, there is arranged an igniting heat source 2 at a predetermined level from the oil surface. The igniting heat source 2 may comprise a nozzle from which a gas is generated. Then, a testing flame is produced at nozzle tip of the igniting heat source 2. Two electrodes 3 and 4 each being made of a ring-shaped wire are arranged above the sample vessel 1. These ring-shaped wire electrodes 3 and 4 are arranged concentrically with each other at a substantially middle level between the oil surface and the igniting heat source 2. One of the electrodes 3 is connected to the ground potential via the sample vessel 1. The electrodes 3 and 4 are connected to a current amplifier 5.

When the heating device is energized, the sample oil S in the sample vessel 1 is gradually heated to initiate an evaporation. A mixture of an oil vapor and an air is ignited by the testing flame generated from the igniting heat source 2 to produce a flame. Then, a flame ion current flows between the two electrodes 3 and 4. The thus generated flame ion current is amplified by the current amplifier 5 to detect the ignition of said mixture gas. A flash point of the sample oil S may be determined as a temperature at which the above mentioned ignition current is detected.

In the known flash point measuring apparatus shown in FIG. 1, the ring-shaped wire electrodes 3 and 4 are used to detect the flame ion current. There have been proposed various kinds of the electrodes for this purpose. However, these known electrodes have rather complicated structure. This is mainly due to the fact that in any case there are required two electrodes. Therefore, the arrangement of the electrodes is very critical. For instance, if the position of the electrodes 3 and 4 with respect to the igniting heat source 2 is deviated from a desired position, the flame ion current could not be detected although the flame is produced. Moreover, the electrodes 3 and 4 are provided between the surface of the sample oil S and the igniting heat source 2, and therefore the vapor of the oil might be prevented by the electrodes 3 and 4 from positively arriving at the igniting heat source 2. Furthermore, when the sample oil S is thermally expanded, the sample oil might be brought into contact with the electrodes 3 and 4 and the flame ion current could not be detected any more.

SUMMARY OF THE INVENTION

The present invention has for its object to provide a useful and novel apparatus for measuring a flash point of an article, in which the above mentioned problems of the known apparatus can be mitigated and the apparatus can be simple in construction by using the igniting heat source as a flame ion current detecting electrode.

According to the invention, an apparatus for detecting a flash point of an article comprises:

a sample vessel containing a sample article and made of an electrically conductive material;

a heating means for heating the sample article contained in the sample vessel;

a temperature detecting means for detecting a temperature of the sample article contained in the sample vessel;

an igniting heat source for igniting a vapor of the sample article, said igniting heat source including an electrically conductive member made of an electrically conductive material; and a flame ion current detecting circuit connected to said sample vessel and electrically conductive member of said igniting heat source to detect a flame ion current flowing between said sample vessel and the electrically conductive member of the igniting heat source; whereby a flash point of the sample article is measured as a temperature of the sample article detected by said temperature detecting means at which the flame ion current is detected by said flame ion current detecting circuit.

In the flash point measuring apparatus according to the invention, when the sample article contained in the sample vessel is heated by the heating means to produce a vapor of the sample article, and when a mixture of said vapor of the sample article and an air is ignited by said igniting heat source to produce a flame ion current which flows between the electrically conductive sample vessel and the electrically conductive member of the igniting heat source. The thus produced flame ion current is detected by the flame ion current detecting circuit. Therefore, a flash point of the sample article can be measured as a temperature of the sample article when the flame ion current is detected by said flame ion current detecting circuit.

BRIEF EXPLANATION OF THE DRAWINGS

FIG. 1 is a schematic view showing a known apparatus for detecting a flash point of an article; and FIG. 2 is a schematic view illustrating an embodiment of the flash point measuring apparatus according to the invention.

DESCRIPTION OF THE PREFERABLE EMBODIMENT

FIG. 2 is a schematic view showing an embodiment of the flash point measuring apparatus according to the invention.

A sample vessel 11 is placed on a platform 16 made of an electrically insulating material and a sample S is contained in the sample vessel. According to the invention, the sample vessel 11 is made of an electrically conductive material such as a metal. In the present embodiment, the sample vessel 11 is formed as an open type having a wide upper opening which is not closed by a lid. Below the sample vessel 11, there is arranged a heating device 17 for heating the sample S contained in the sample vessel. In the present embodiment, the heating device 17 is formed by an electric heater including a filament. But according to the invention, various kinds of heating devices such as a gas burner may be equally used.

There is provided a temperature detecting probe 12 which is held by a suitable stand placed on the platform 16 such that a tip of the temperature detecting probe 12 is immersed in the sample S contained in the sample vessel 11.

Above the sample vessel 11, there is arranged an igniting heat source 13 at a predetermined level from the sample surface. The igniting heat source 13 is held by a support 14 such that the igniting heat source 13 can be moved in a horizontal plane. In the present embodiment, the igniting heat source 13 comprises a gas nozzle made of an electrically conductive material and a test flame is generated at a nozzle tip of the igniting heat source 13. According to the invention, the igniting heat source 13 may be formed by an electrically heating filament. The igniting heat source 13 serves as an anode electrode and the sample vessel 11 serves as a cathode electrode. These electrodes are connected to a current amplifier 15 such that a flame ion current flowing between these electrodes, i.e. between the sample vessel 11 and the igniting heat source 15 can be detected.

After supplying the sample S in the sample vessel 11 up to a standard level mark provided on the vessel, air bubbles produced on the surface of the sample S are removed. Then, the igniting heat source 15 is ignited to produce a test flame. The test flame is adjusted to have a size corresponding to a standard fire ball. According to the ASTM, the heating device 17 is energized to increase a temperature of the sample S contained in the sample vessel 11 at a rate of 14°–17° C./min. After a temperature of the sample S has arrived at a point which is lower than an expected flash point of the sample S by 28° C., then the sample S is heated at a slower rate such as 5.5°±0.5° C./min.

After a temperature of the sample oil S has arrived at a point which is lower than an expected flash point of the sample S by 28° C., each time a temperature of the sample S is increased by 2° C., the igniting heat source 13 is moved along an arc of a circle which passes a center the sample vessel 11 and having a radius not less than 150 mm, a line connecting a middle point of the arc and a center of the circle passing through a point above the temperature detecting device 12. In this manner, the surface of the sample S is scanned by the igniting heat source 13 for about one second. During this scanning, when a mixture of a sample vapor and an air is ignited by the test flame, there is instantaneously produced a flame. Then, a flame ion current flows between the sample vessel 11, i.e. cathode electrode and the igniting heat source 13. This flame ion current is detected and amplified by the amplifier 15, and a temperature of the sample S at this time is detected as a flash point of the sample S.

The above mentioned embodiment of the flash point measuring apparatus according to the invention operates in accordance with the Cleveland open-type flash point test method defined under D92. It should be noted that the present invention may be equally applied to the Pensky-Martens closed-type flash point testing method defined under D93, in which an upper opening of a sample vessel is covered with a lid having a small opening and the test flame is inserted through the opening of the lid into an inside space surrounded by the sample vessel and lid each time the temperature of the sample S increased by 1° C. or 2° C.

In the flash point measuring apparatus according to the invention, the igniting heat source 13 and sample vessel 11 are used as the anode electrode and cathode electrode, respectively, and thus it is no more necessary to provide any separate electrode and the apparatus can be simple in construction. Moreover, the igniting heat source 13 serves as both the heat source for generating the test flame and the electrode for detecting the flame ion current, and therefore the flame ion current can be detected positively without being interference by the electrode.

Furthermore, in the flash point measuring apparatus according to the invention, it is not necessary to arrange any electrode above the surface of the sample S, and therefore the evaporated sample can arrive at the igniting heat source 13 without being interfered by the electrode. Moreover, the sample S might not be brought into contact with the electrode although the sample is thermally expanded, and thus a detection error can be prevented.

The present invention is not limited to the embodiment explained above, but many modifications and alternations may be conceived by those skilled in the art within the scope of the invention. For instance, the igniting heat source 13 may be formed an electric heating filament. Then, the heating filament may be simply connected to the current amplifier 15. This modification can be widely used in any flash point measuring method defined under D92. Further, the igniting heat source 13 may be moved automatically by means of an electric motor and a suitable driving mechanism. Moreover, the temperature detecting device 12 may be formed by an electric temperature detecting device. In this case, an output signal of the electric temperature detecting device may be supplied to a control circuit, to which is also supplied an output signal of the current amplifier 15.

As explained above in detail, in the flash point measuring apparatus according to the invention, the sample vessel and igniting heat source are used as the electrodes for detecting the flame ion current. Therefore, it is no more required to provide a separate electrode and the construction of the apparatus becomes simple. Moreover, the flame ion current can be detected positively owing to the fact that a sample vapor can be positively brought into contact with the igniting heat source without being interfered by the electrode.

What is claimed is:

1. An apparatus for measuring a flash point of an article comprising:
    a sample vessel containing a sample article and made of an electrically conductive material;
    a heating means for heating the sample article contained in the sample vessel;
    a temperature detecting means for detecting a temperature of the sample article contained in the sample vessel;
    an igniting heat source for igniting a mixture of a vapor of the sample article and an air, said igniting heat source including an electrically conductive member; and adapted to scan a surface of the sample article and
    a flame ion current detecting circuit connected to said sample vessel and electrically conductive member of said igniting heat source to detect a flame ion current flowing between said sample vessel and said electrically conductive member of the igniting heat source; whereby a flash point of the sample article is measured as a temperature of the sample article detected by said temperature detecting means at which the flame ion current is detected by said flame ion current detecting circuit.

2. An apparatus according to claim 1, wherein said igniting heat source comprises a nozzle made of an electrically conductive material, said nozzle being connected to said flame ion current detecting circuit, and a test flame is generated from a tip of said nozzle.

3. An apparatus according to claim 1, wherein said sample vessel is formed to have a wide upper opening and said igniting heat source is arranged movably in a horizontal plane such that a surface of the sample article is scanned by said igniting heat source.

4. An apparatus according to claim 3, wherein said igniting heat source is moved in said horizontal plane along an arc passing a center of the sample vessel.

* * * * *